(12) United States Patent
McAninch (10) Patent No.: US 6,813,026 B2
(45) Date of Patent: Nov. 2, 2004

(54) PURGE SYSTEM FOR OPTICAL METROLOGY TOOL (75) Inventor: Jeffrey E. McAninch, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 233 days.

(21) Appl. No.: 10/027,385

(22) Filed: Dec. 21, 2001

(65) Prior Publication Data
US 2002/0149774 A1 Oct. 17, 2002

Related U.S. Application Data (60) Provisional application No. 60/283,115, filed on Apr. 11, 2001, and provisional application No. 60/336,854, filed on Nov. 1, 2001.

(51) Int. Cl.$^7$ .................. G01N 21/55; G01N 21/47; G01N 21/21
(52) U.S. Cl. .................. 356/445; 356/369; 356/446
(58) Field of Search .................. 356/369, 445–448, 356/237.1, 237.2–237.5

(56) References Cited

U.S. PATENT DOCUMENTS

| | | | | |
|---|---|---|---|---|
| 4,277,177 A | * | 7/1981 | Larsen et al. | 356/431 |
| 4,824,248 A | * | 4/1989 | Neumann | 356/244 |
| 6,151,116 A | * | 11/2000 | Hirosawa | 356/369 |
| 6,414,302 B1 | * | 7/2002 | Freeouf | 356/369 |
| 6,628,397 B1 | * | 9/2003 | Nikoonahad et al. | 356/445 |

* cited by examiner

*Primary Examiner*—Richard A. Rosenberger
(74) *Attorney, Agent, or Firm*—Stallman & Pollock LLP (57) ABSTRACT

A purge system for an optical metrology tool is disclosed. The metrology tool includes an optics plate for supporting the measurement optics. A movable stage supports a wafer below the optics plate. Inert purge gas is injected between the lower surface of the optics plate and the upper surface of the wafer. The gas flow functions to stabilize and homogenize the ambient in the measurement region. The gas flow also serves to clear the measurement area of absorbing species which is particular useful for measurements using vacuum ultraviolet light.

54 Claims, 11 Drawing Sheets

PURGE SYSTEM FOR OPTICAL METROLOGY TOOL

PRIORITY CLAIM:

The present application claims priority to U.S. Provisional Patent Applications Ser. No. 60/283,115, Apr. 11, 2001, and Ser. No. 60/336,854, filed Nov. 1, 2001, both of which are incorporated herein by reference

TECHNICAL FIELD

The subject invention relates to optical metrology devices which require a controlled ambient atmosphere to improve measurement. More specifically, the invention relates to an optical metrology instrument that includes a gas-flow system for the purpose of purging the optical path to stabilize measurement and clear the path of optically absorbing species.

BACKGROUND OF THE INVENTION

The semiconductor industry is presently developing photolithographic methods utilizing 157 nm wavelength laser light as the next step in the continuing reduction of device length scales. Metrology tools are presently needed to support this development, for instance by providing measurements of the optical properties of candidate materials over the spectral range from ~140 to ~200 nm. These wavelengths lie within a region known as the vacuum ultraviolet (VUV), in which the high absorption coefficients of oxygen and water vapor lower the attenuation length in standard air to fractions of a millimeter. (Historically, this light could only be observed under vacuum conditions, hence the designation.) Achieving the transmission and stability necessary for a VUV optical metrology tool, in which the optical paths are 0.5–2 m, therefore requires oxygen and water concentrations in the low parts-per-million (ppm) range averaged over the entire optical path. In the near future, as production facilities incorporating 157 nm lithography come online, larger numbers of these tools—capable of handling production line throughput—will be required. A major engineering challenge in the development of 157 nm metrology is simultaneously providing high wafer throughput and low optical absorption.

In the prior art, Freeouf, in U.S. Pat. No. 6,222,199 B1, incorporated herein by reference, teaches the benefits of performing specular bi-directional ellipsometric measurements in a geometry where the entire light path is maintained in a controlled ambient to prevent absorption and local excitation. At present, multiple commercial manufacturers offer VUV spectroscopic ellipsometer (SE) products that maintain a controlled ambient via housing the entire metrology apparatus inside a sealed container filled (purged) with purified nitrogen gas.

A design that places the complete instrument in a sealed container has two notable disadvantages. First, the purged volume is significantly larger than the volume that encloses the VUV optical path alone and must house multiple components—e.g., optical elements, optical mounts, electrical components, electrical wiring, actuators, adhesives, etc.—which do not need to be in the purged atmosphere. This places stringent and overly restrictive requirements on component materials since component and material outgassing can degrade the purge environment. Furthermore, a high volume purge-gas flow is required to cool the system electronics. Second, the system requires some sort of sealable entry port or load-lock to enable sample (wafer) insertion while preventing the introduction of oxygen and water vapor contaminants into the chamber. This necessarily hinders wafer handling and substantially reduces throughput and usability.

Accordingly it would be desirable to provide a VUV metrology tool architecture wherein the purged volume is minimized—approaching the volume of the VUV optical path—and the instrument does not require a load-lock to isolate either the sample (wafer) or the metrology tool from the laboratory environment.

SUMMARY OF THE INVENTION

The subject invention relates to a VUV optical metrology system that incorporates a gas-purge of the optical path—the light path that connects the illuminator, the sample and the detector. The metrology system avoids the use of a continuous, solid, barrier to separate the optical path from the laboratory environment; therefore, no load-lock is required. A substantially oxygen and water-vapor free environment is created and maintained by hydrodynamic flow of purified inert purge-gas that is introduced at least one injection point along the optical path.

The flow acts to displace optically adsorbing contaminants from the optical path, remove optically absorbing species from the surfaces bounding the optical path and, inhibit back diffusion of the chemical contaminants displaced in the flow. The purge-gas flow simultaneously prevents back-diffusion of atmospheric constituents from the laboratory environment to the optical path. This is achieved using a geometrical arrangement where the system optics is maintained in a housing that has a substantially planar surface.

The measurement process is initiated by raising the wafer from a load position to a measurement position where the wafer surface is substantially parallel to the housing surface where light is incident on the wafer at a measurement location. In the measurement position the volume bounded by the wafer and the housing approximates a thin disk. The flow system is arranged such that purge-gas is injected into the bounded volume at flow sufficient to purge the bounded volume in the vicinity of the measurement location. The purge gas flows outward from the measurement location and is exhausted at the wafer boundary.

The subject purge system will also improve measurements at longer wavelengths. More specifically, the purge system will help to stabilize temperature and make measurements conditions more uniform. This will lead to more accurate and repeatable measurements.

DETAILED DESCRITPION OF THE PREFERRED EMBODIMENTS

Figure 1:
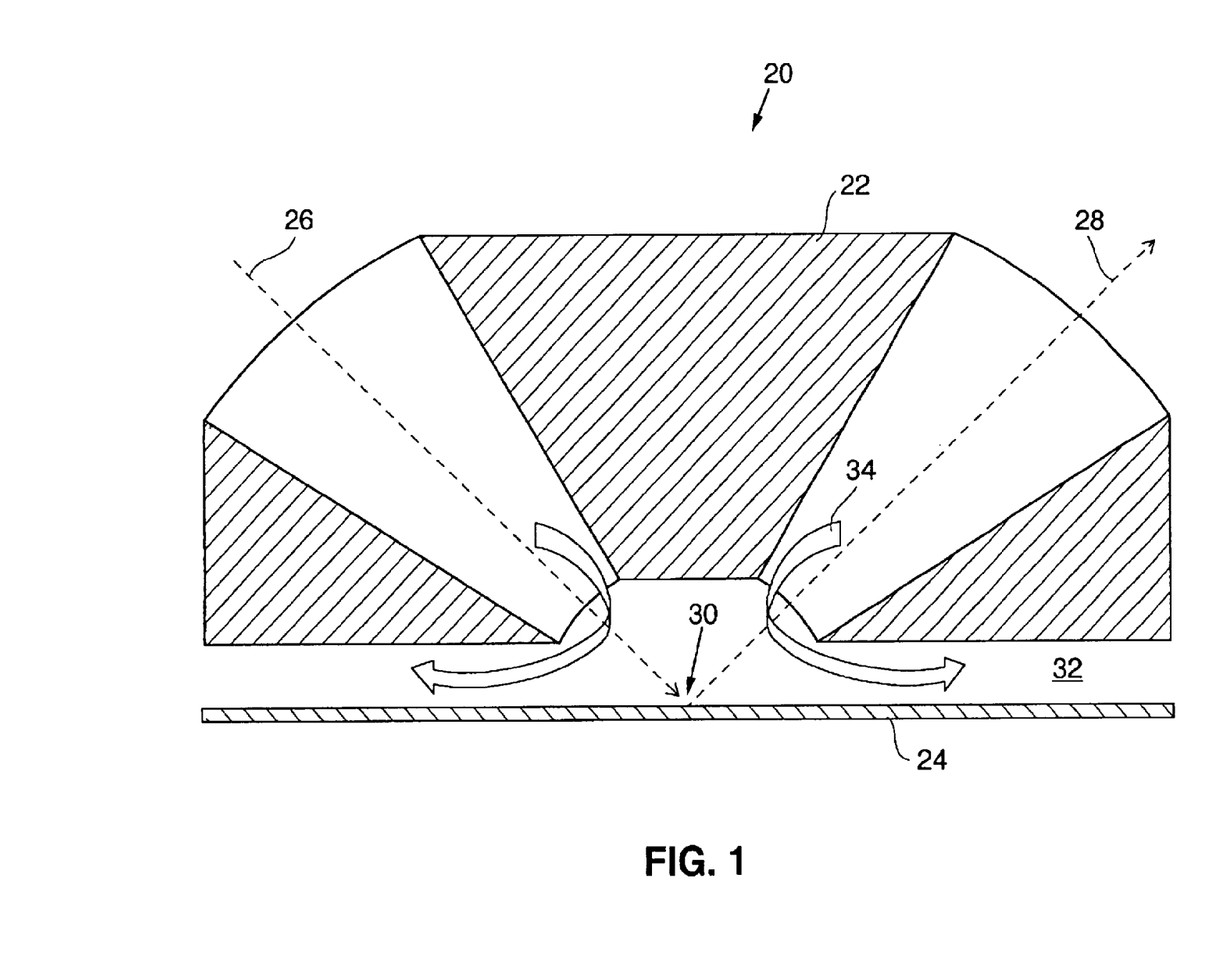
FIG. 1 illustrates a preferred embodiment for purging of the optical path.

FIG. 1 depicts a cross sectional view of an optical metrology system 20 that implements a preferred embodiment of the inventive gas-purge scheme. The figure depicts a portion of the optics housing 22 that contains two cylindrical beam transport tubes that serve to transmit the incident 26 and reflected 28 radiation. Wafer 24 is illustrated at the measurement position where incident illumination 26 interacts with wafer 24 at measurement location 30. Reflected radiation 28 is transmitted to a detection system that is not shown in the figure. As illustrated in the figure the lower surface of optics housing 22 is substantially planar so that the volume 32 bounded by the lower surface of housing 22 and wafer 24 approximates a thin plate.

A flow of high purity purge gas 34 is injected upstream and flows through a beam tube toward measurement location 30. The flow is exhausted at the periphery of wafer 24. For VUV applications the purge gas must be substantially transparent in the spectral region between 140 and 175 nm. Suitable gases would include nitrogen, helium and argon. For high purity applications preferred sources include the boil-off from cryogenic liquids and cylinders of ultra-pure compressed gas. The purge gas is injected into the system at or somewhat above atmospheric pressure.

Figure 2A:
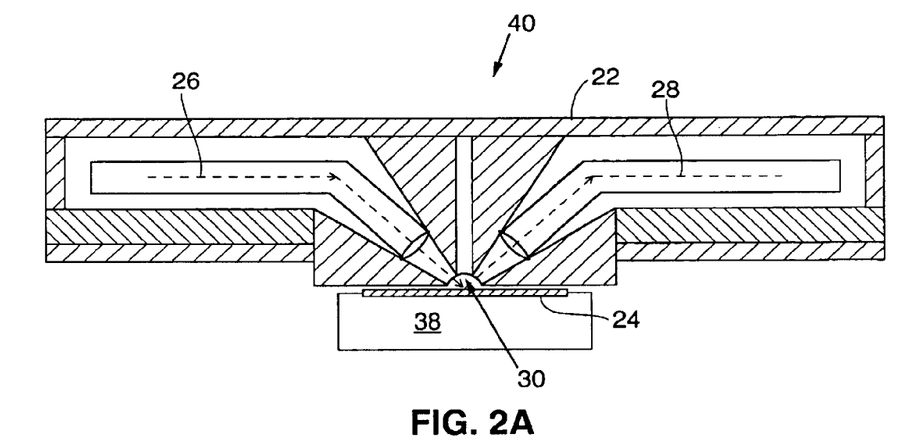
FIGS. 2a–2b schematically illustrate the layout of an optical metrology tool where the optics housing isolated from the sample space (2a), and the purge-gas flow (2b) in the measured region.
Figure 2B:
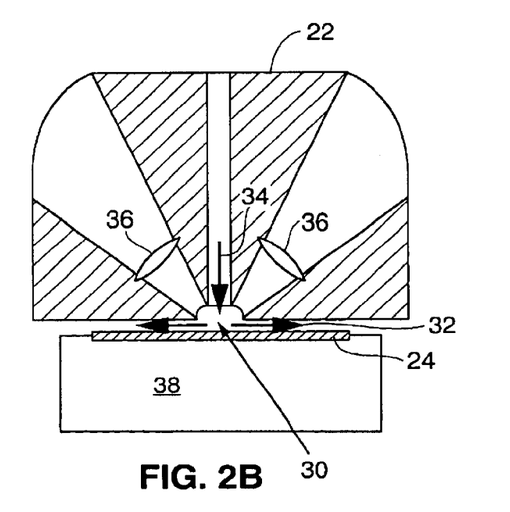
Figure 3:
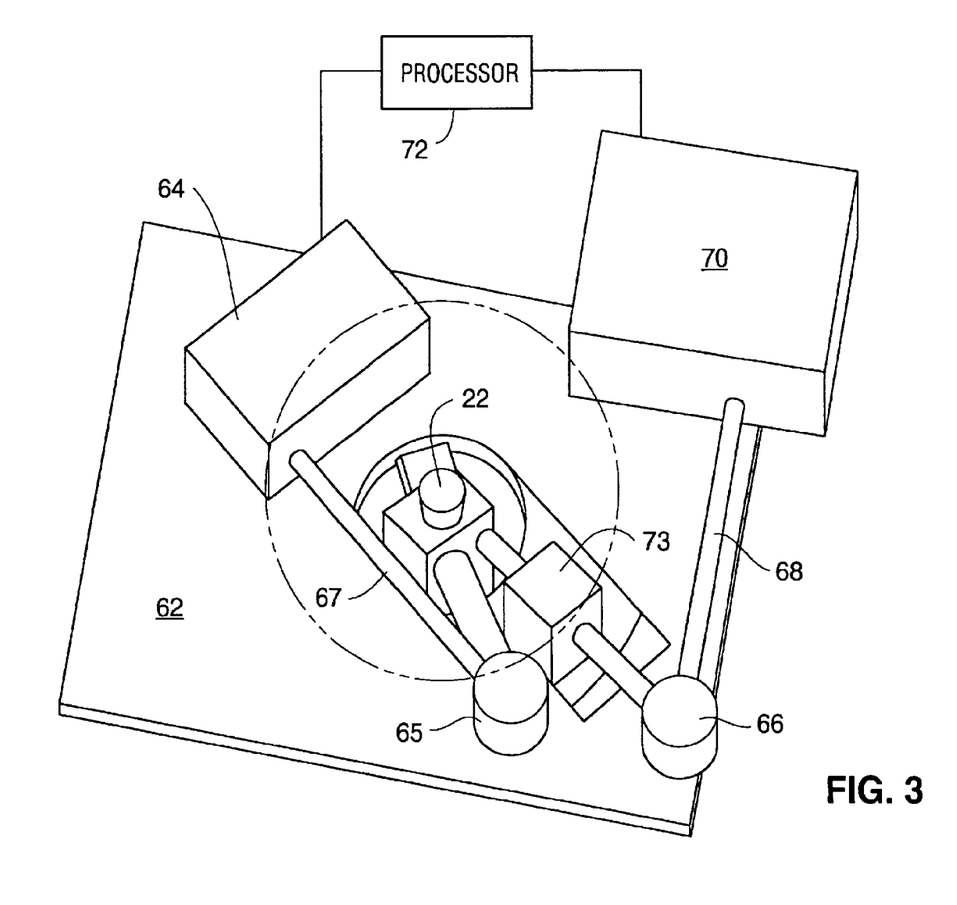
FIG. 3 illustrates an embodiment of a gas-purged optical metrology instrument.
Figure 4:
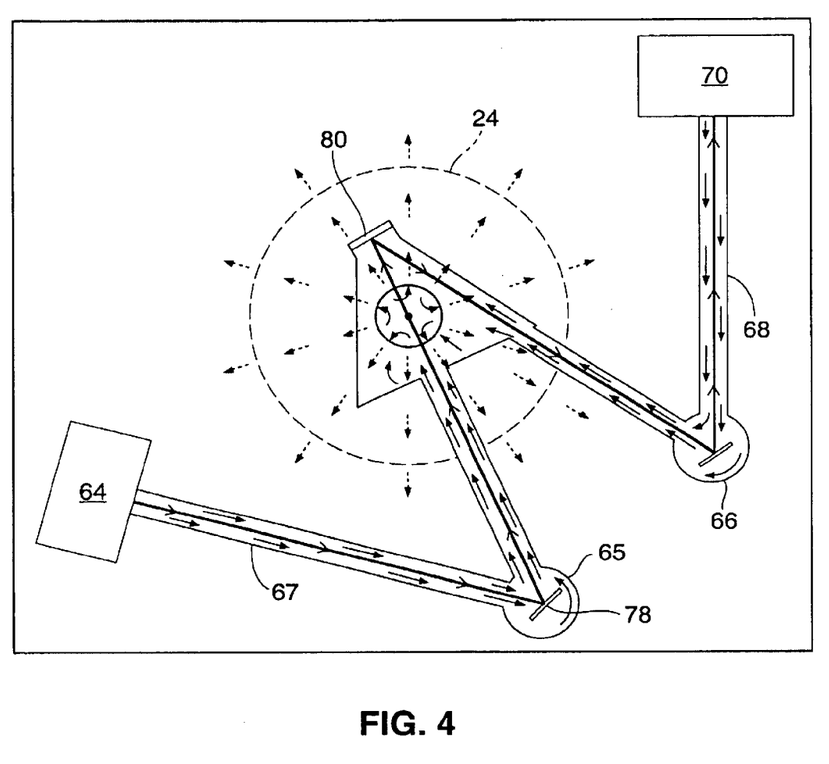
FIGS. 4 is a plan projection illustrating the flow of the purge gas through the instrument.
Figure 5:
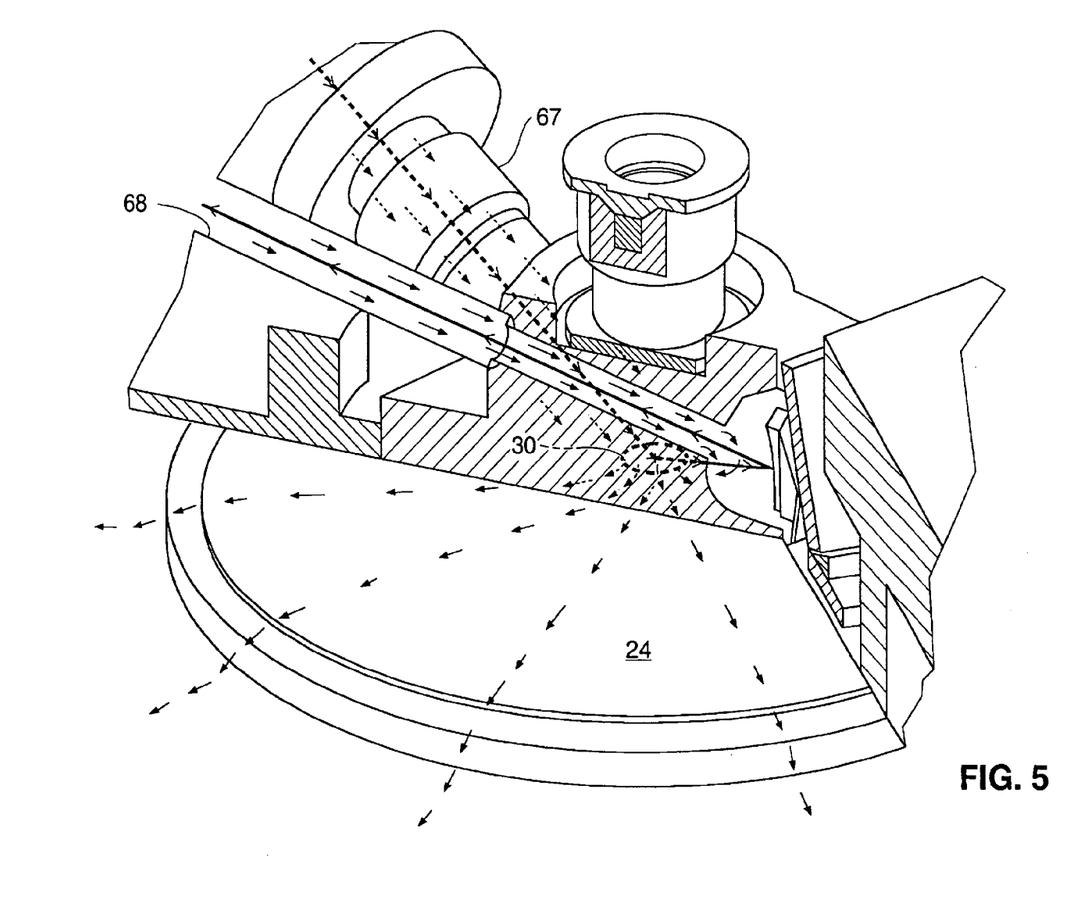
FIG. 5 is a perspective view, partially in section of the gas-purged metrology instrument of the subject invention.
Figure 6:
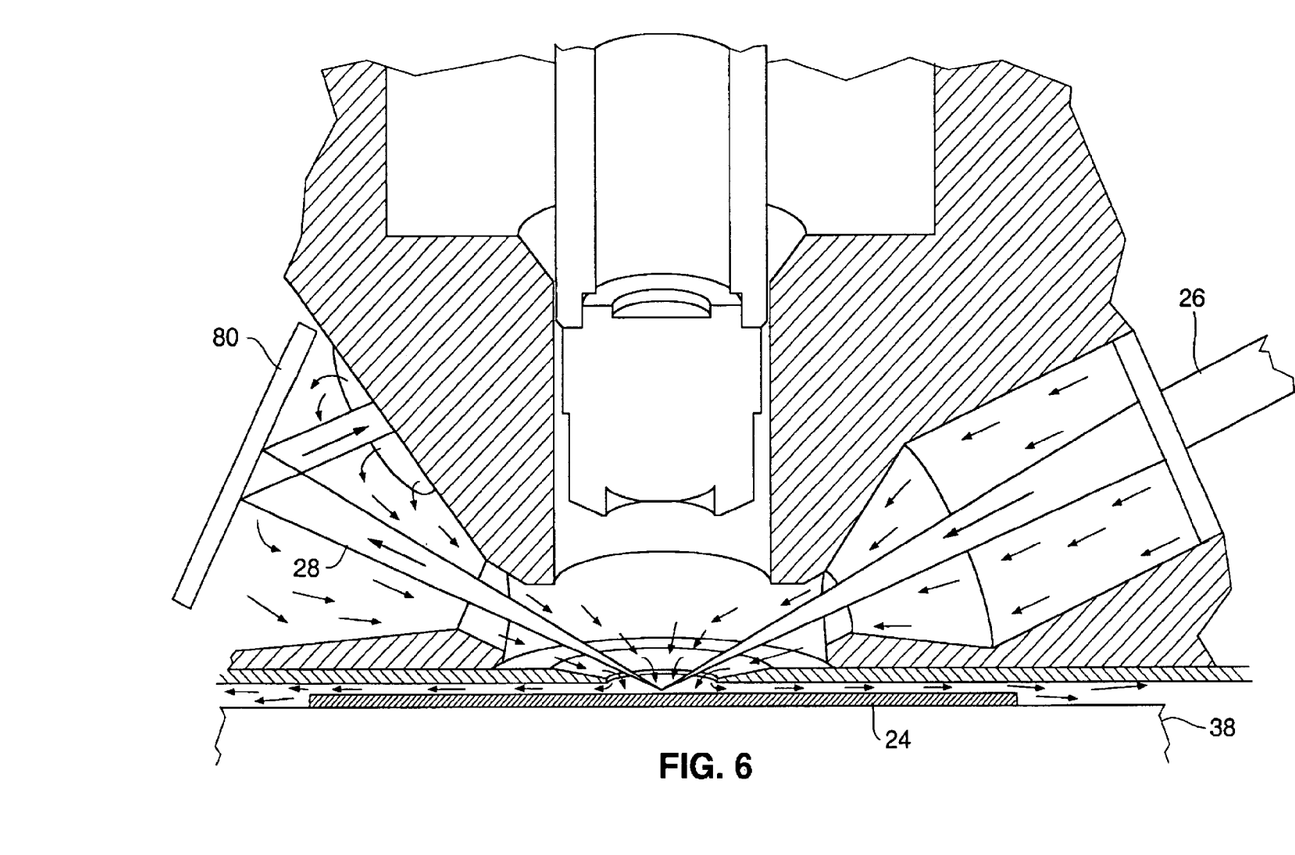
FIG. 6 is an enlarged, cross-sectional view of the gas-purged metrology instrument of the subject invention.

FIGS. 2a–2b schematically illustrate the layout of an optical metrology tool 40 where lenses 36 isolate the interior of optics housing 22 from bounded volume 32. FIG.(2a) illustrates a schematic layout of the system and further includes wafer transport assembly or stage 38 which serves both to move wafer 24 between wafer-load and wafer-measurement positions, and to sequentially locate multiple locations of the wafer surface at measurement location 30, so that a plurality of sites on the wafer surface may be measured. Here the interior of optics housing 22 is isolated from the sample and the laboratory environment by lenses 36. The isolation could be accomplished by installation of a variety of optical components including lenses, windows, polarizing elements, transmissive elements, diffractive elements and optical systems containing reflective components. Furthermore the optical systems must efficiently transmit VUV radiation and therefore be fabricated from VUV transmissive material such as fused silica, fluorine-doped fused silica, quartz, $CaF_2$, $SrF_2$, $BaF_2$, $MgF_2$, $LaF_3$ and LiF. Consequently, only the volume bounded by the exterior surfaces of lenses 36, optics housing 22 and wafer 24 requires dynamic gas-purging. FIG. 2b is a magnified view of the region surrounding measurement position 30. In this case the injection point is located between the beam tubes and the purge gas flow 34 is exhausted at the periphery wafer 24.

FIGS. 3 to 6 illustrate a preferred embodiment of a gas-purged spectroscopic ellipsometer. The system incorporates optics plate 62, optics housing 22, illuminator 64, sealed housings 65, 66, beam-transport tubes 67, 68, spectrometer/detector assembly 70 and processor 72. In the commercial embodiment, a rotating compensator is located in housing 73. Wafer transport assembly 38 and wafer 24 are below optics plate 62 and are not visible in the figure. Beam-transport tubes 67, 68 and housings 65, 66 are utilized to separate the optical path from the laboratory environment. In the preferred embodiment housings 65, 66, illuminator assembly 64 and spectrometer/detector assembly 70 include ports for vacuum pumping and gas purging the enclosures. Where needed, electrical feed-throughs are included. In the preferred embodiment beam transport tubes 67, 68 housings 65, 66, illuminator assembly 64, spectrometer/detector assembly 70 and optics housing 22 are purged by a flow of high purity $N_2$.

Illuminator 64 can include one or more light sources. In one preferred embodiment, a 50 W VUV-grade $D_2$ discharge-lamp is utilized for measurement wavelengths between 140 and 400 nm, and a W lamp is used for wavelengths between 400 and 850 nm. Alternative embodiments may incorporate a single, broad band source or narrow band sources including lasers, lamps and amplified stimulated emission sources. Light from the illuminator is transmitted through beam-transport tube 67 to housing 65 where it is turned by mirror towards the sample. The incident illumination is polarized and focused (by a lens and polarizer, not shown) onto the wafer surface where it reflects from and interacts with the surface of sample 24.

The reflected radiation is turned by mirror 80 and is collected and transmitted through beam-transport tube 68 to housing 66 and spectrometer/detector assembly 70 to analyze the polarization state change in the incident illumination produced by reflection from and interaction with sample 24. Processor 72 serves to automate the measurements and analyze the output signals generated by spectrometer/detector assembly 70.

The design elements for gas-purging the optical paths illustrated in FIGS. 3 to 6 can be implemented in a broad variety of optical metrology tools including spectroscopic ellipsometers, spectroscopic reflectometers, spectroscopic polarized beam reflectometers, scatterometers and optical CD measurement tools. Furthermore, multiple instruments can be combined on a common platform to comprise a single broad-band optical metrology instrument that incorporates multiple spectroscopic metrology capabilities, e.g. reflectometry, scatterometry and reflectometry. Here it is particularly advantageous to provide a processor to analyze the output signals generated by the various detectors. In the preferred embodiment the analysis protocols can treat the output signals individually or in combination to evaluate the characteristics of a sample. The detector outputs may include signals corresponding to changes in magnitude, changes in polarization state, changes in magnitude of polarized radiation and scatter, that result from the interaction with and reflection of illumination reflected from the sample, measured at a plurality of wavelengths.

Prior to initiating a detailed mechanical design for the proof-of-principle SE tool, a finite element model analysis simulator was employed to model the dynamic purge system performance and simulate the purging process in a prototype tool design. A fully 3D model was developed using the commercially available finite-element package FloWorks. FloWorks functions as an add-in to SolidWorks, a standard mechanical design package, so that mechanical drawings of the prototype design could be computer generated. The intent of the model was to permit a parametric study of flow system performance as a function of the design variables assessing the temporal evolution and temporal stability of chemical purity, flow geometry, and gas temperature as a function of boundary shape and flow rate. The stability against perturbations, time required for the initial purge, time scales for recovery from wafer exchange, and the variation in system performance as a function of wafer position (wafer edge exclusion) were determined.

The embodiment shown in FIGS. 3 to 6 was used in the simulation. FIGS. 7a–7c and 8a–8c illustrate the time evolution (a: 1 sec, b: 5 sec, c: 10 sec) of the $O_2$ concentration and gas temperature as a function of position across a 2-d slice of the bounded volume within the measurement region following a wafer load that occurs at time, t=0.

The initial conditions used in the simulation assumed a 300 mm diameter wafer located 1 mm below the bottom of the optics plate with the measurement location 3 mm from the wafer edge. The initial chemical composition within the bounded volume was a mixture of 80% $N_2$ and 20% $O_2$ (room air) at a pressure of 1 atm and a temperature of 28 C. Solids surfaces were maintained at a fixed temperature of 30 C. A continuous flow of $N_2$ purge gas is injected into the bounded volume at t=0, at flow rate of 500 standard cubic centimeters per minute (sccm), at 28 C., at 3 injection points: one along each of the spectroscopic ellipsometer light paths 26 and 28, the outer purge, and one through a fitting placed near the auto-focus system 82, the central purge. In the simulations, a back-flow of room air at 1000 sccm is injected at the wafer boundary to account for back-diffusion of room-air toward the measurement region. The total flow is exhausted at the wafer boundary into a reservoir of room air at 1 atm and 20 C.

Figure 7A:
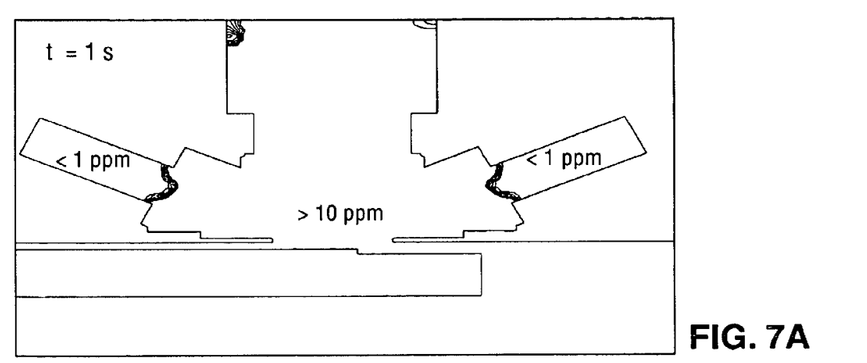
FIGS. 7a–7c illustrate the results of a finite-element computer model for the time evolution of the gas composition in the vicinity of the measurement region following sample exchange.
Figure 7B:
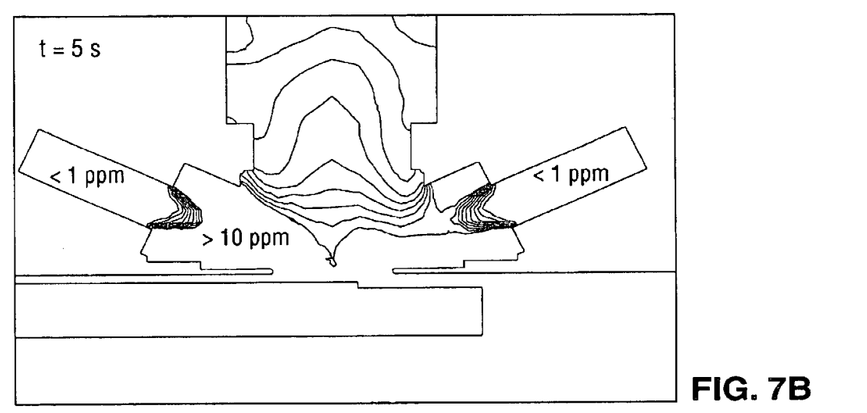
Figure 7C:
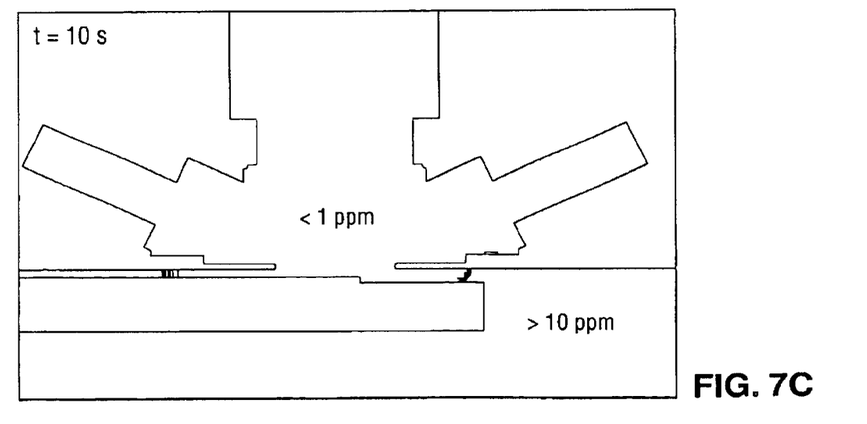

FIGS. 7a–7c illustrate the results of a finite-element computer model for the time evolution of the gas composition in the vicinity of the measurement region of the prototype system following sample exchange. The model utilized the initial conditions and parameters described in the preceding paragraph. FIGS. 7a–7c show the gradient in $O_2$ concentration, in a 2-d plane passing through the measurement location, 1, 5 and 10 sec after sample exchange. The $O_2$ concentration is reduced to below 20 ppm within 10 sec. Consequently, the bounded volume is essentially free of optically absorbing species 10 sec following wafer exchange. The model simulations predict that high-throughput VUV optical metrology can be performed in a system without the requirement for a solid physical barrier between the measured region and the laboratory environment.

Figure 8A:
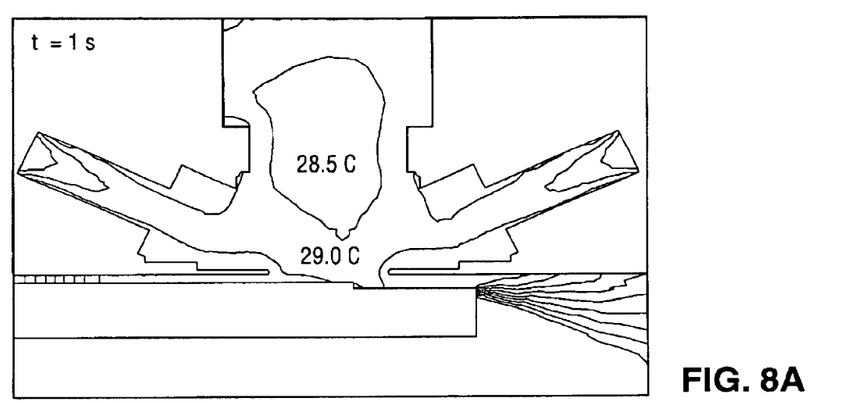
FIGS. 8a–8c illustrate the results of a finite-element computer model for the time evolution of the gas temperature in the vicinity of the measurement region following sample exchange.
Figure 8B:
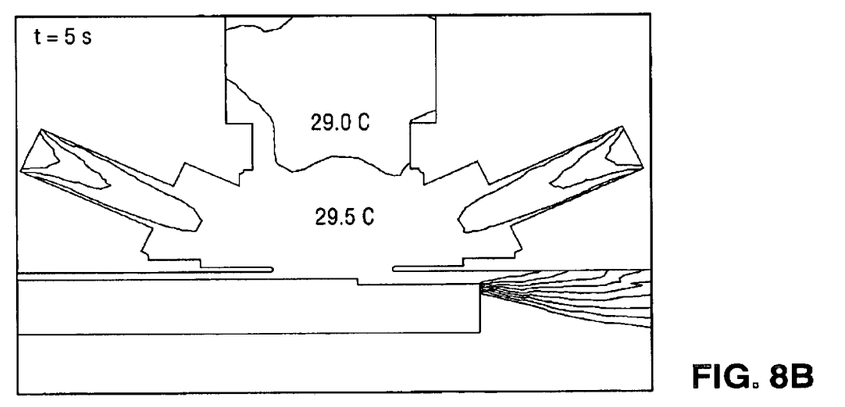
Figure 8C:
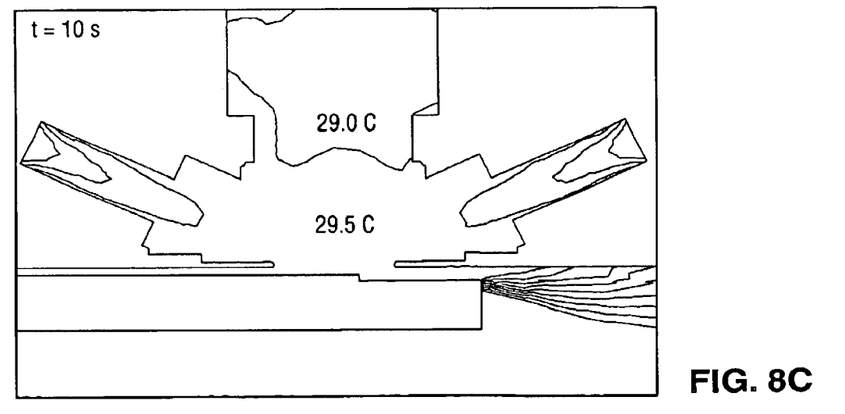

In high performance optical metrology it is essential to minimize thermal excursions in the optical system, particularly those induced in the vicinity of the wafer following wafer exchange. Thermal variations in the ambient surrounding the measurement region can produce spatial inhomogeneity of the refractive index of the ambient that comprises the optical path, confusing the measurement and complicating the analysis. FIGS. 8a–8c illustrate the evolution of the gas temperature within the measurement region of the prototype system following sample exchange. The model utilized the initial conditions and parameters described above. FIGS. 8a–8c show the gradient in temperature, in a 2-d plane passing through the measurement location, 1, 5 and 10 sec after sample exchange. The gas is thermally equilibrated within 5 sec throughout the key measurement region. Consequently, the simulations predict that the limitations on wafer throughput imposed by the purge approach are chemical rather than thermal.

A number of additional simulations were undertaken to establish the parametric variation of the system performance on the design variables. The simulations were computationally intensive, e.g. the generation of time-dependent results illustrate in FIGS. 7 and 8 required ~48–72 hrs of processing time on a 1 GHz Pentium III with 1 GB of RAM. The output files required ~6 GB of disk space. In aggregate the simulations reveal:

a) Simpler designs for the purge orifice and surrounding area work better. Attempts to be clever by shaping surfaces always seemed to increase the flushing times and required larger flows to get the same exclusion of room air. The final design essentially brought the metal as close as was reasonable to the optical path.

b) Flow velocities of 20–30 cm/s were sufficient in the model to block intrusion of room air into the measurement area at the level required for VUV-SE. These velocities are well within the laminar flow regime for the spatial scales involved.

c) For a 1 mm gap between the wafer and optics plate, 20–30 cm/s flow velocities can be obtained in the vicinity the purge orifice when flow rate is ~1000 sccm.

d) Flushing times to reach <20 ppm $O_2$ over the entire optical path were ~10 s when the central volume was filled with room air.

e) At the required flow, pressure gradients in the system are small.

f) At the required flow, the purge gas thermally equilibrates rapidly.

g) Flow rates of ~1000 sccm through the purge orifice are sufficient to maintain low ppm $O_2$ levels even with the wafer removed.

A VUV spectroscopic ellipsometer (VUV-SE) was designed and implemented utilizing the above described simulation results. The VUV-SE instrument was based on the assignee's Opti-Probe OP5300 frame and optics plate. This choice simplified the design and construction. A pre-existing OP7300 optics plate was adapted to the VUV requirements, and placed into a pre-existing OP5300 frame. The VUV-SE optical path, enclosed and purged, was designed to fit within this platform. The design minimized the purged volume and was capable of supporting a vacuum of $<1\times10^{-6}$ atm to facilitate pump-purge "clean-up" of the enclosed space following exposure of the system to the atmosphere. Consequently, all of the VUV optical components, the VUV light source, VUV spectrometer, turning mirrors, Rochon polarizer and analyzer, and waveplate stepper motor are placed in O-ring sealed housings. Lids are removable for access, and have ports for pumping, purge inlet and outlet, and electrical feedthroughs. Beam tubes (16 mm or 25 mm clear apertures) are used to enclose the optical path between housings.

An Alcatel Drytel pump is used for evacuating the system. This oil-free molecular drag pump with diaphragm backing pump is designed for clean room use, and can be exhausted into the room. A mechanical vacuum gauge is used for monitoring rough pump-down and let-up, and an Alcatel Cold Cathode/Pirani gauge is used for measuring lower pressures. Commercial O-ring fittings (Kwik-Flange, Swagelok, and Quick-Disconnect) are used for tube-tube and tube-housing attachments, and to assemble the external gas handling system. A plate with a captured O-ring was fabricated to cover the purge orifice from below (with the stage in the load position), allowing the entire system to be pumped out.

The primary $N_2$ supply is house nitrogen gas (boil-off from liquid nitrogen) although bottled gas can be used. To prevent residual contamination (chronic or acute) in this supply from reaching the purge system, the $N_2$ is passed through a custom two-stage purifier purchased from Innovative Technologies. The first stage of the purifier is an activated carbon molecular sieve that removes trace volatile organics. The second stage is a reduced copper powder column to remove water and oxygen. Both stages can be regenerated in house. The $N_2$ flow to the VUV tool is controlled using a multi-port manifold with fine flow adjust, flow meters and 0.5 $\mu$m point-of-use filters. Gas is transported from the manifold to the tool using $\frac{1}{8}$" Teflon tubing connected with stainless steel Swagelok fittings.

Figure 9:
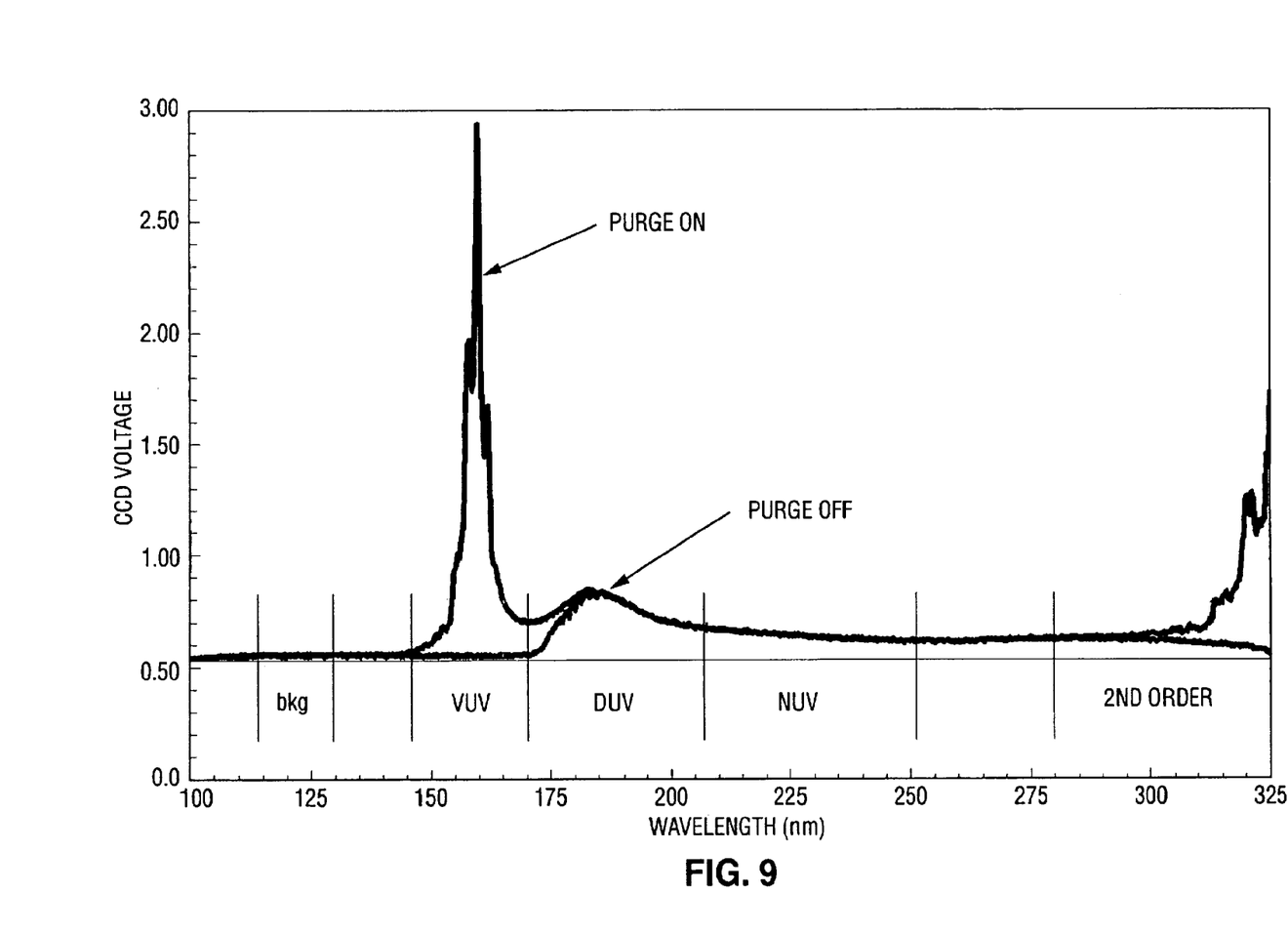
FIG. 9 shows the wavelength dependent detector output illustrating the influence of the gas purge on detector signal in the VUV, DUV and NUV spectral regions.
Figure 10:
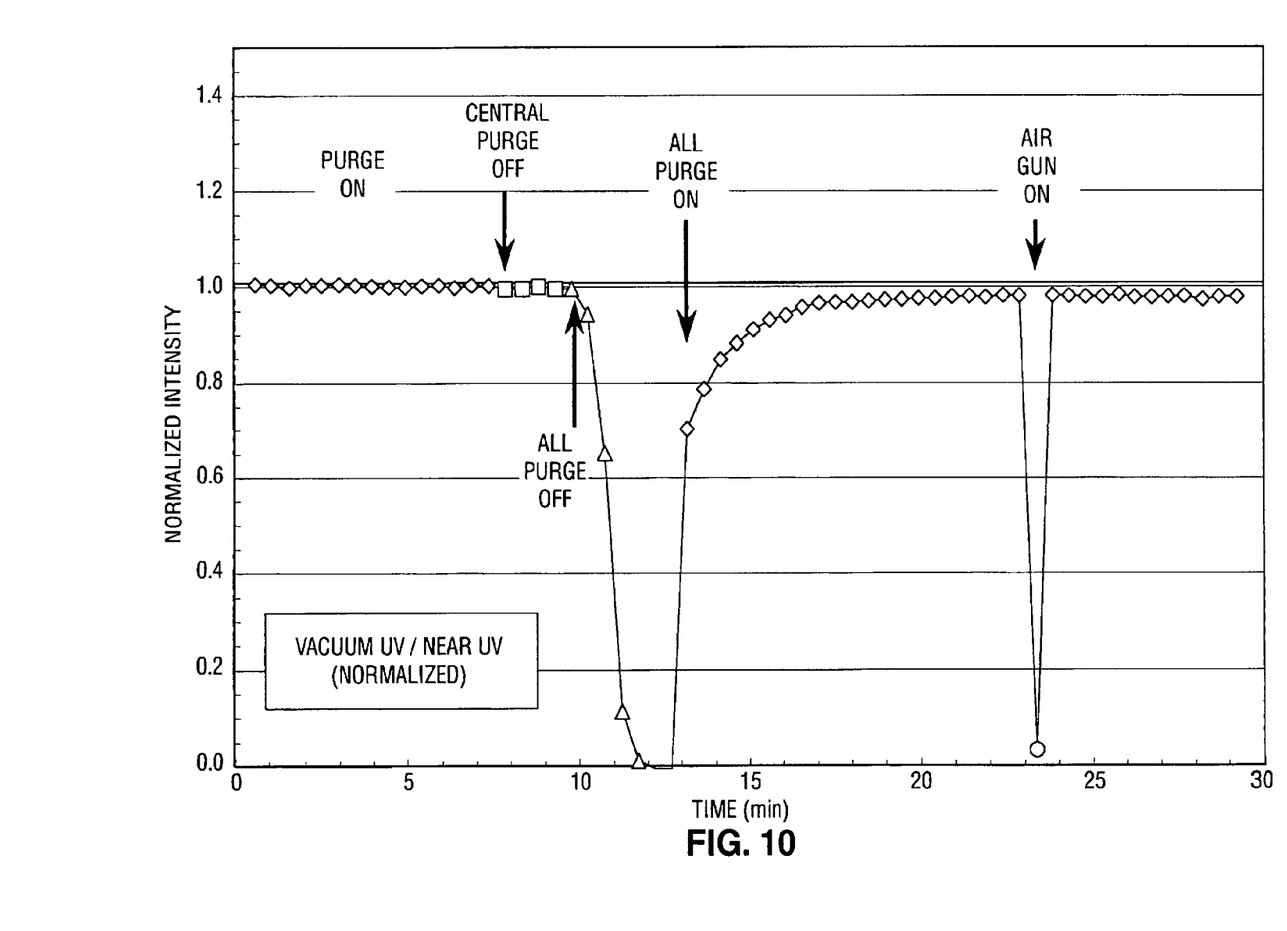
FIG. 10 illustrates the time evolution of the detector output following interruption of the purge-gas stream.
Figure 11:
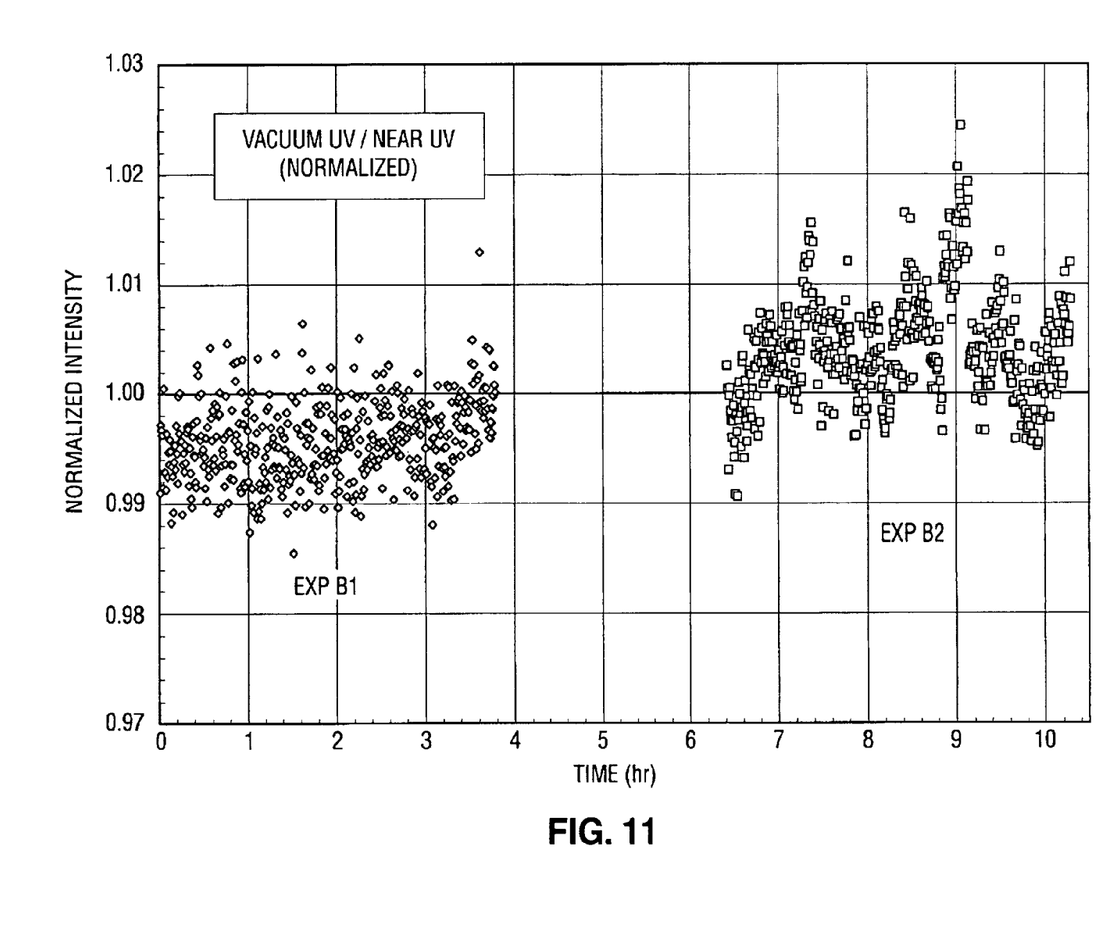
FIG. 11 illustrates the measured temporal stability and reproducibility of the VUV and NUV signals following repetitive wafer load/unload cycles.

FIGS. 9, 10 and 11 show the results of a series of experiments performed on the VUV-SE system. In these experiments, UV spectra were recorded with the wafer located at several different wafer positions as a function of purge-gas flow rate. System performance (efficiency of purging) was evaluated by comparing the time evolution of the detected VUV light intensity to the detected near UV (NUV) intensity as function of flow rate. As describe below and illustrated in FIG. 9 the purge flow has a marked influence on VUV transmission but a negligible effect in the NUV spectral range. Consequently, the ratio of the normalized VUV/NUV intensity is a good quantitative measure of the effect of the purge on optical transmission.

Referring to FIG. 9, the measured detector signal (CCD Voltage) is plotted vs. wavelength over a wavelength region between 100 and 325 nm. Spectra were taken with a 1024 windowless CCD array detector with 16 averages per read with the purge on (red) and off (blue). In the spectral range spanning ~200–250 nm, which we refer to as the NUV, the purge has no observable effect on the detector signal. However, in the spectral range spanning ~150–175 nm, which we refer to as the VUV, the purge has a marked influence. In the absence of the purge, the light is fully attenuated by atmospheric absorption and the CCD voltage, corrected for background noise, is 0. With the purge on the CCD generates a large signal (3 Volts peak).

FIG. 10 illustrates the effect of perturbing the purge gas flow on the optical transmission. The normalized intensity ratio (VUV/NUV) is plotted as a function of time for various operating conditions. The wafer was placed with the measurement location coincident with the wafer center, the purge gas flow was initiated and system was optically focused. Spectra were recorded approximately every 30 s. At t=8 minutes the central purge was stopped. This had a negligible effect on the VUV transmission. At t=10 minutes the outer purge flow was terminated. This had an immediate effect on VUV transmission and the VUV signal dropped to 0 at t=13.5 minutes. At this time both central and outer purge flows were resumed. The VUV transmission took 5–7 min to recover to ~98% of it's initial value. At t=20 minutes we attempted to inject a transient pulse of air into the bounded volume near the wafer edge. The transient pulse was generated with an air gun driven compressed $N_2$ operated in room air—the gun creates a Venturi action so that the bulk of the nozzle output is room air. It proved difficult to produce an observable effect. At 23 min the gun was moved to ~1 ft from the edge of the wafer-chuck, and angled upward to deflect the air off the lower surface of the optics housing and into the bounded volume between the optics housing and the wafer surface. The gun was operated for ~30 s until the next spectrum was recorded. The air-gun affected signals throughout the VUV, DUV and NUV; however, the detection system fully recovered within 30s of turning-off the air-gun.

FIG. 11 illustrates the measured temporal stability and reproducibility of the VUV and NUV signals following repetitive wafer load/unload cycles. Repeat measurement cycles were made at the wafer center. A measurement cycle encompassed the following steps a) maintain the wafer at load the load position for 30 s.

b) move the wafer to the measurement position with the measurement location at the wafer center c) focus the optical system d) record a number, n, of consecutive spectra e) return the wafer to the load position In order to address any systematic variation in sensitivity of the spectral response to focus repeatability, the measurements were split into 2 sub-experiments, B1 and B2. In B1, the focus was re-established prior to recording each spectrum. In B2, the focus was established initially, and frozen while the subsequent spectra were recorded. For experiment B1, n=25, for B2 n=27. As illustrated in FIG. 11, the time evolution of the normalized VUV/NUV intensity ratio is both independent of time and, within the experimental inaccuracies, independent of focusing protocol.

In the preferred embodiment, the wafer transport system 38 (FIG. 2) includes a vacuum chuck for holding the wafer in place. The chuck is, in turn, mounted upon two or more movable stages for positioning the wafer with respect to the measurement spot. Common stage combinations include full X and full Y stages, ½ X and ½ Y plus rotary (theta) stages and polar coordinate stages (R, theta). In the preferred embodiment, the stage arrangement will include the ability move the chuck in the vertical or Z axis. In the wafer load position, the chuck is lowered an amount sufficient so the wafer can be easily loaded on top of the chuck. Once the wafer is loaded, the stage will raise the chuck to bring the wafer into close proximity to the bottom surface of the optics plate. Preferably, the separation between the wafer and the optics plate will be between 10 microns and 2 millimeters.

In the preferred method of the subject invention, the purge flow is initiated prior to or during the time the chuck is being raised into the measurement position. Raising the chuck into the measurement position while the purge gas is flowing helps to drive absorbing species out of the measurement area. More specifically, as the chuck is raised and the wafer comes into close proximity to the bottom surface of the optics plate, the gas in the region will be squeezed outwardly and replaced by the purge gas. In this manner, the region around the measurement spot will be rapidly cleared of the absorbing species, allowing a measurement to be taken relatively quickly after the wafer is in the measurement position.

The present invention has utility beyond operation in the VUV measurement wavelength range. More specifically, the initial experiments demonstrate that the subject approach functions to provide a stable, homogenous environment for measurement. More specifically, the environment around the measurement area is composed of a known, homogenous purge gas at a controlled and stable temperature. This condition leads to far greater precision and repeatability of the measurement. Accordingly, the use of the subject invention may be warranted for measurement in any wavelength region where greater precision and repeatability is desired.

As seen in the figures, in the preferred embodiment, the primary purge gas flow is directed down towards the wafer near the measurement area. The flow incoming is directed radially inwardly and down to the wafer. When the flow strikes the wafer, it is turned and passes over the wafer in a radially outward direction.

It is within the scope of the broader aspects of the subject invention to provide any flow path for the purge gas which causes the gas to pass over the measurement area. For example, the purge gas can be initiated on one side of the wafer and passed across the wafer in a curtain-like fashion. The flow path should be arranged so that it passes the measurement area.

While the subject invention has been described with reference to a preferred embodiment, various changes and modifications could be made therein, by one skilled in the art, without varying from the scope and spirit of the subject invention as defined by the appended claims.

What is claimed:

1. An arrangement for use in an optical metrology instrument where light is detected and analyzed after reflecting from a measurement position on a sample comprising:

an optical system connected to a support, the support including a faceplate having an exterior surface that is substantially planar and faces the sample, said faceplate further including at least one aperture for transmitting the incident and reflected light between the optical system and the measurement position;

a stage arranged such that the sample surface is substantially parallel to the faceplate and configured such that multiple locations on the sample surface can be sequentially located at the measurement position, the separation between the faceplate and the sample being arranged such that during measurement the volume bounded by the faceplate and the sample surface approximates a thin plate; and an apparatus for maintaining a purge-gas flow within said bounded volume, comprising:

a source of purge-gas; and means for introducing said purge-gas at an injection point within the bounded volume and arranged so that a purge gas flow directed toward the measurement position travels substantially radially away from the measurement position and is exhausted at a periphery of the sample in order to purge a measurement region including the measurement position where the light is reflected.

2. The arrangement of claim 1 where the optical metrology instrument includes one or more elements selected from the group consisting of reflectometers, ellipsometers, polarized beam reflectometers, scatterometers and optical CD metrology instruments.

3. The arrangement of claim 1 where the optical system contains at least one element selected from the group consisting of transmissive, reflective, diffractive and polarizing optics.

4. The arrangement of claim 1 where said aperture further contains at least one substantially transparent optical element for the purpose of isolating said system optics from said bounded volume.

5. The arrangement of claim 4 where said substantially transparent optical element is fabricated from at least one optical material selected from the group consisting of fused silica, fluorine-doped fused silica, quartz, $CaF_2$, $SrF_2$, $BaF_2$, $MgF_2$, $LaF_3$ and LiF.

6. The arrangement of claim 1 where the purge-gas is selected to be substantially non-absorptive over the wavelength range of the light employed in the optical metrology instrument.

7. The arrangement of claim 1 where the purge-gas is selected from the group consisting of helium, argon and nitrogen.

8. The arrangement of claim 1 where said source of purge-gas is selected from the group consisting of compressed gases and cryogenic liquids.

9. The arrangement of claim 1 where said purge-gas is introduced above atmospheric pressure.

10. The arrangement of claim 1 where the separation between the faceplate and sample surface during measurement is selected to minimize the time required to purge that portion of the bounded volume surrounding the measurement position.

11. The arrangement of claim 1 where the separation between the faceplate and the sample surface during measurement is in the range between 1 $\mu$m and 2 mm.

12. The arrangement of claim 1 wherein said means for introducing the purge gas includes at least one fluid channel formed in the faceplate and communicating with the source of purge gas, said fluid channel having an outlet adjacent to the measurement position so that the flow path is established in the bounded volume adjacent the measurement position and radially outwardly therefrom.

13. A method for gas-purging an optical metrology instrument that measures the changes in incident illumination produced by interaction with and reflection from a sample at a measurement position, said instrument including system optics mounted to a support, said support including a faceplate separating the system optics from the sample to be measured, said faceplate having a planar surface and at least one aperture for the purpose of transmitting incident and reflected light between the sample and the system optics at said measurement position, said instrument further including a stage for supporting the sample below the optics plate, said method comprising the steps of:

establishing a flow of purge-gas through the faceplate toward the sample;

raising the sample stage to said measurement location such that the volume bounded by the faceplate and sample approximates a thin plate, said flow of purge-gas traveling through said bounded volume toward the measurement position then passing substantially radially away from the measurement position and being exhausted at a periphery of the sample in order to purge a measurement region including the measurement position;

illuminating the sample at said measurement position; and detecting and analyzing the illumination following reflection from and interaction with the sample at said measurement position.

14. The method of claim 13 where said aperture further contains at least one substantially transparent optical element for the purpose of isolating said system optics from said bounded volume.

15. The method of claim 14 wherein said at least one substantially transparent optical element is fabricated from at least one optical material selected from the group consisting of fused silica, fluorine-doped fused silica, quartz, $CaF_2$, $SrF_2$, $BaF_2$, $MgF_2$, $LaF_3$ and LiF.

16. A method of claim 13 wherein the optical metrology instrument includes at least one element selected from the group consisting of reflectometers, ellipsometers, polarized beam reflectometers, scatterometers and optical CD metrology instruments.

17. The method of claim 13 where the incident illumination originates from at least one light source selected from the group consisting of broad-band and narrow-band light sources.

18. The method of claim 17 where the broad-band and narrow-band light sources are selected from the group consisting of incandescent, discharge, amplified stimulated emission and laser sources.

19. The method of claim 17 where the incident illumination spans at least a portion of at least one of the extreme ultra-violet, deep ultra-violet, ultra-violet, visible, near infra-red and infra-red spectral ranges.

20. The method of claim 13 where the system optics contain at least one element selected from the group consisting of transmissive, reflective, diffractive and polarizing optics.

21. The method of claim 13 where the purge-gas is selected to be substantially non-absorptive over the wavelength range of the illumination employed in the optical metrology instrument.

22. The method of claim 13 where the purge-gas is selected from the group consisting of helium, argon and nitrogen.

23. The method of claim 13 where the purge-gas source is selected from the group consisting of compressed gases and cryogenic liquids.

24. The method of claim 13 where said purge-gas is introduced above atmospheric pressure.

25. The method of claim 13 where the separation between the faceplate and sample surface at said measurement location is selected to minimize the time required to purge the bounded volume.

26. The method of claim 13 where the separation between the faceplate and the sample surface at said measurement location is in the range between 10 $\mu$m and 2 mm.

27. A method as recited in claim 26 wherein the purge gas is injected adjacent the measurement position and flows radially outwardly therefrom.

28. The method of claim 13 where the purge-gas is introduced into the bounded volume adjacent the measurement position with said purge gas traveling radially outwardly therefrom.

29. An apparatus for evaluating characteristics of a sample comprising:
   a light source for illuminating a sample;
   an optical system mounted to a support, said support including a faceplate, with an exterior surface that is substantially planar and faces the sample, said faceplate further including at least one aperture for the purpose of transmitting the incident and reflected light from the source between the optical system and the measurement position;
   a stage arranged such that the sample surface is substantially parallel to the planar faceplate and with the separation between the faceplate and the sample being arranged such that during measurement the volume bounded by the faceplate and the sample surface approximates a thin plate;
   an apparatus for maintaining a purge-gas flow within said bounded volume, comprising:
      a source of purge-gas; and
      a conduit for introducing said purge-gas at an injection point within the bounded volume adjacent the measurement position and arranged so said purge-gas is directed toward the measurement position and allowed to flow away from the measurement position to be exhausted at a periphery of the sample in order to purge a measurement region including the measurement position;
   a detection system for monitoring light reflected from the sample in the purged measurement region and generating output signals in response thereto; and
   a processor for evaluating the characteristics of the sample based on the detected output signals.

30. The apparatus of claim 29 where the light source is selected from at least one element from the group consisting of broad-band and narrow-band light sources.

31. The apparatus of claim 29 where the emission spectrum of the light source spans at least a portion of at least one of the extreme ultra-violet, deep ultra-violet, ultra-violet, visible, near infra-red and infra-red spectral ranges.

32. The apparatus of claim 29 where light source includes at least one element selected from the group consisting of incandescent, discharge, amplified stimulated emission and laser sources.

33. The apparatus of claim 29 where the detection system includes at least one element selected from the group consisting of reflectometers, ellipsometers, polarized beam reflectometers, scatterometers and optical CD metrology tools.

34. The apparatus of claim 33 wherein the detection system is selected from the group consisting of: spectroscopic reflectometers for measuring the change in magnitude of the radiation at a plurality of wavelengths and spectroscopic ellipsometers for measuring the change in polarization state of the radiation at a plurality of wavelengths.

35. The apparatus of claim 34 wherein the detection system is a polarized beam spectroscopic reflectometer for measuring the change in magnitude of polarized radiation at a plurality of wavelengths.

36. The apparatus of claim 29 wherein the detection system and processor operate to analyze, individually or in combination, output signals selected from the group consisting of: the change in magnitude of the radiation at a plurality of wavelengths, the change in polarization state of the radiation at a plurality of wavelengths, the change in magnitude of polarized radiation at a plurality of wavelengths.

37. The apparatus of claim 29 where the purge-gas is selected to be substantially non-absorptive over the wavelength range of the light employed in the optical metrology instrument.

38. The apparatus of claim 29 where the purge-gas is selected from the group consisting of helium, argon and nitrogen.

39. The apparatus of claim 29 where the purge gas is supplied by one or more elements selected from the group consisting of compressed gases and cryogenic liquids.

40. The apparatus of claim 29 where the purge-gas is introduced above atmospheric pressure.

41. The apparatus of claim 29 where the separation between the faceplate and sample surface is selected to minimize the time required to purge that portion of the bounded volume surrounding the measurement position.

42. The apparatus of claim 29 where during measurement the separation between the faceplate and the sample surface is in the range between 10 $\mu$m and 2 mm.

43. An arrangement for use in an optical metrology instrument where light is detected and analyzed after reflecting from a measurement position on a sample comprising:
   an optical system mounted to a support, said support including a faceplate having an exterior surface that is substantially planar and faces the sample, said faceplate further including at least one aperture for transmitting the incident and reflected light between the optical system and the measurement position, said faceplate further including a fluid channel having an output adjacent the aperture;
   a stage arranged such that the sample surface is substantially parallel to the faceplate and configured such that multiple locations on the sample surface can be sequentially located at the measurement position, the separation between the faceplate and the sample being arranged such that during measurement the volume bounded by the faceplate and the sample surface approximates a thin plate; and a source of inert purge-gas coupled to the fluid channel of the faceplate for establishing a flow of purge gas directed toward and allowed to flow from the the measurement position, the flow of purge gas then being exhausted at a periphery of the sample in order to nurse a measurement region about the measurement position.

44. An inspection module for use in an optical metrology device, said metrology device including a source for generating a probe beam of radiation that is directed to a spot on a semiconductor wafer, said module comprising:

a top plate having a planar bottom surface and an aperture configured to permit the probe beam to pass therethrough from the upper surface thereof, said top plate further including a fluid channel having an inlet and an outlet, with the outlet being located near the position on the wafer to be measured by the probe beam;

a translatable bottom plate having a planar top surface for supporting the wafer and being movable from a lower loading position to an upper measuring position, and wherein when the bottom plate is in the upper measuring position a narrow gap is defined between the upper surface of the wafer and the lower surface of the top plate; and a source of inert purge gas coupled to the inlet of the fluid channel and wherein said channel is configured such that when said purge gas is passed therethrough a flow path is established toward the measurement spot on the wafer and then radially outwardly therefrom to purge a measurement region including the measurement spot.

45. An inspection module as recited in claim 44 wherein said aperture is sealed with an optical element substantially transparent to the probe beam radiation.

46. A method of optically inspecting a semiconductor wafer with a metrology tool, said tool including a stage for supporting a wafer below a planar optics plate, said planar optics plate including at least one aperture for allowing a probe beam generated from a light source located above the optics plate to illuminate and reflect off the wafer at a measurement position, said method comprising the steps of:

positioning the stage with respect to the optics plate so a narrow gap is defined between the bottom surface of the optics plate and the upper surface of the wafer;

injecting a purge gas through the planar optics plate and into the narrow gap adjacent the measurement position such that the purge gas is directed toward the measurement position then allowed to flow radially therefrom whereby the purge gas is exhausted at the periphery of the wafer such that a measurement region including the measurement position is purged; and optically inspecting the wafer at the measurement position with the probe beam.

47. A method as recited in claim 46 wherein said step of injecting purge gas is initiated prior to the positioning step.

48. A method as recited in claim 46 wherein said purge gas is injected into the narrow gap through a fluid channel formed in the optics plate.

49. An apparatus for evaluating characteristics of a sample comprising:

a light source for illuminating a sample;

a support structure, said light source being connected to the support structure, the support structure including a faceplate, with an exterior surface that is substantially planar and faces the sample, said faceplate further including at least one aperture for the purpose of transmitting the incident and reflected light from the measurement position;

a detector connected to the housing for monitoring light reflected from the sample and generating output signals in response thereto;

a first hollow member through which light from the source is channeled to the aperture in the face plate;

a second hollow member through which light reflected from the sample is channeled from the aperture in the face plate to the detector;

a stage arranged such that the sample surface is substantially parallel to the planar faceplate and with the separation between the faceplate and the sample being arranged such that during measurement, the volume bounded by the faceplate and the sample surface approximates a thin plate; and a source of purge-gas, said purge gas being directed through the hollow members and also introduced within the bounded volume adjacent the measurement position so that substantially all of the light path between the light source and the detector is purged.

50. The apparatus of claim 49 where the purge-gas is selected to be substantially non-absorptive over the wavelength range of the light from said light source.

51. The apparatus of claim 49 wherein the faceplate includes at least one fluid channel communicating with the source of purge gas, said fluid channel having an outlet adjacent to the measurement position so that the flow path is established in the bounded volume adjacent the measurement position and radially outwardly therefrom.

52. A method for gas-purging an optical metrology instrument that measures the changes in incident illumination produced by interaction with and reflection from a sample at a measurement position, said instrument including system optics mounted to a support, said support including a faceplate separating the system optics from the sample to be measured, said faceplate having a planar surface and at least one aperture for the purpose of transmitting incident and reflected light between the sample and the system optics at said measurement position, said instrument further including a stage for supporting the sample below the optics plate, said method comprising the steps of:

establishing a flow of purge-gas below the optics plate adjacent the aperture;

raising the sample stage to said measurement location such that the volume bounded by the faceplate and sample approximates a thin plate, said flow of purge-gas traveling through said bounded volume toward the measurement position then radially outwardly from the measurement position in order to puree a measurement region including the measurement position;

illuminating the sample at said measurement position; and detecting and analyzing the illumination following reflection from and interaction with the sample at said measurement position.

53. The method of claim 52 where said aperture further contains at least one substantially transparent optical element for the purpose of isolating said system optics from said bounded volume.

54. The method of claim 52 where the purge-gas is selected to be substantially non-absorptive over the wavelength range of the illumination employed in the optical metrology instrument.

* * * * *